(12) United States Patent
Tockstein et al.

(10) Patent No.: US 8,904,887 B2
(45) Date of Patent: Dec. 9, 2014

(54) RADIO FREQUENCY TRANSPARENT THERMAL WINDOW

(75) Inventors: Michael A. Tockstein, Long Beach, CA (US); James P. Nokes, Torrance, CA (US); Jon V. Osborn, Thousand Oaks, CA (US); Dhruv N. Patel, Cerritos, CA (US); Alan R. Hopkins, Los Angeles, CA (US); John S. Williams, Palos Verdes Estates, CA (US); Gary N. Harper, El Segundo, CA (US)

(73) Assignee: The Aerospace Corporation, El Segundo, CA (US)

( * ) Notice: Subject to any disclaimer, the term of this patent is extended or adjusted under 35 U.S.C. 154(b) by 309 days.

(21) Appl. No.: 13/299,095

(22) Filed: Nov. 17, 2011

(65) Prior Publication Data
US 2013/0125676 A1 May 23, 2013

(51) Int. Cl.
*G01N 17/00* (2006.01)
*B64G 7/00* (2006.01)

(52) U.S. Cl.
CPC *G01N 17/00* (2013.01); *B64G 7/00* (2013.01); *G01N 17/002* (2013.01)
USPC ........................................................ 73/865.6

(58) Field of Classification Search
None
See application file for complete search history.

(56) References Cited

U.S. PATENT DOCUMENTS

| | | | | |
|---|---|---|---|---|
| 3,352,122 A * | 11/1967 | Rothenberg et al. | ........... | 62/55.5 |
| 3,437,260 A * | 4/1969 | Gilmour, Jr. | .................... | 417/49 |
| 4,550,979 A * | 11/1985 | Meier | ........................... | 359/896 |
| 5,863,376 A * | 1/1999 | Wicker et al. | ............ | 156/345.38 |
| 2004/0195403 A1 * | 10/2004 | Atterbury et al. | ............. | 239/690 |
| 2007/0001910 A1 * | 1/2007 | Yamanaka et al. | ..... | 343/700 MS |
| 2011/0115380 A1 * | 5/2011 | Ebe et al. | ................. | 315/111.41 |

* cited by examiner

*Primary Examiner* — Robert R Raevis
(74) *Attorney, Agent, or Firm* — Fulwider Patton LLP

(57) ABSTRACT

A radio-frequency transparent window having internal conduits for the passage of cooling fluid is configured for simulating a highly uniform thermal environment for testing a device intended for use in space. The device to be tested is placed within a chamber in which a vacuum condition is maintained by a radio-frequency transparent pressure window under a pressure seal. Within the chamber, the thermal window is positioned adjacent, but not in contact with, the pressure window. A radio frequency signal is capable of passing directly through both the thermal window and the pressure window to permit communication with the device being tested within the housing. The thermal window is not in contact with the device so there in no conduction of heat from the device. Radiant heat transfer may occur from the device to the thermal window.

18 Claims, 8 Drawing Sheets

RADIO FREQUENCY TRANSPARENT THERMAL WINDOW

FEDERALLY FUNDED RESEARCH

This invention was made with government support under Contract No. FA8802-09-C-0001 awarded by the Department of the Air Force. The government has certain rights in the invention.

BACKGROUND

The present invention relates to methods of testing electronic components that are destined to be launched into space as part of suborbital, orbital, or remote spacecraft.

Spacecraft are becoming an ever increasing component of our lives, even if in an indirect way. In addition to the manned spacecraft that are sent to the International Space Station or beyond, there are many unmanned spacecraft that are launched every year including probes sent to deep outer space and distant planets, orbiting weather satellites, orbiting global positioning satellites, and sub-orbital intercontinental missiles that may or may not have a military purpose. Such spacecraft are controlled by complex electronic components that are designed and assembled on earth, but which must be capable of withstanding the extreme environmental conditions of space.

Manufacturers of electronic components for eventual use in spacecraft have developed various methods for simulating space-like conditions here on Earth, into which such electronic components may be inserted during testing. For example, some manufacturers use systems in which a space-like vacuum may be established in a chamber that may also be cooled to space-like temperatures. However, vacuum and thermal chambers typically are made of metal or other conductive substances, and are found to interfere with radio signals passing between the device under test and the reciprocal radio transmitter-receiver outside the chamber when testing the performance of a device with respect to transmission and reception of radio frequency signals via antennae.

There is a need in the art for a chamber suitable for testing electronic components in a space-like environment, that will not only simulate the temperature and pressure conditions of space, but that will permit substantially unimpeded radio communication with the device inside the chamber under test. The present invention addresses these and other needs.

SUMMARY OF THE INVENTION

In a preferred embodiment, the invention includes a chamber for testing electronic devices. The chamber comprises a housing defining an opening through which, initially, components may be inserted. A pressure window is provided, configured to close the opening under a pressure seal, the pressure window being formed of a substantially radio-frequency transparent material. A thermal window is provided and positioned inside the housing adjacent the pressure window. The thermal window defines a system of one or more internal conduits for the passage of cooling fluid, whereby the thermal window itself may be cooled. The thermal window is formed of a substantially radio-frequency transparent material.

The pressure window and the thermal window are positioned in relation to each other such that a radio frequency signal is able to pass directly through both the pressure window and the thermal window into the housing. In a preferred aspect, the substantially radio-frequency transparent material is polycarbonate, and may be formed as a laminate from two sheets that are bonded together. The invention further includes a pump configured to pump air from the housing sufficiently to create a vacuum condition within the housing. In another aspect, the thermal window is capable of being cooled to at least minus 65° C. Further preferably, the one or more internal conduits in the thermal window includes at least two independent conduits wherein cooling fluid in one independent conduit flows in a direction opposite to the flow of cooling fluid in another independent conduit In another facet, the invention is a method of testing. The method comprises positioning a device having an antenna in a chamber having an opening. A cooling element is positioned adjacent the antenna wherein the cooling element is substantially transparent to radio frequency. The opening is closed with a pressure window that is substantially transparent to radio frequency, whereafter the chamber is evacuated to a low pressure. The temperature of the cooling element is lowered by passing a cooling fluid through channels inside the element, thereby cooling the antenna of the device. Finally, radio frequency signals are passed from an antenna outside the chamber, through the pressure window and through the element, to the cooled antenna inside the chamber, thereby, applying test protocols to the device by radio frequency signal. In another aspect of the method, the chamber is positioned adjacent an anechoic chamber so that the opening faces into the anechoic chamber. Furthermore, passing radio frequency signals from an antenna outside the chamber includes passing the radio frequency signals through the anechoic chamber. In a preferred aspect, cooling the cooling element includes cooling the element to at least minus 65° C., and positioning an element adjacent the antenna includes positioning an element that is shaped to conform to the shape of the antenna. Where the antenna is planar, the cooling element has a planar configuration.

DETAILED DESCRIPTION OF THE PREFERRED EMBODIMENTS

With reference to the drawings, there is described a preferred embodiment of a test chamber of a system and method for testing electronic devices that will be used in outer space, the chamber being configured firstly to simulate temperature and pressure conditions found in space, and secondly to permit substantially unimpeded radio communication from outside the chamber with the device under test inside the chamber.

Chamber and Components

Figure 1:
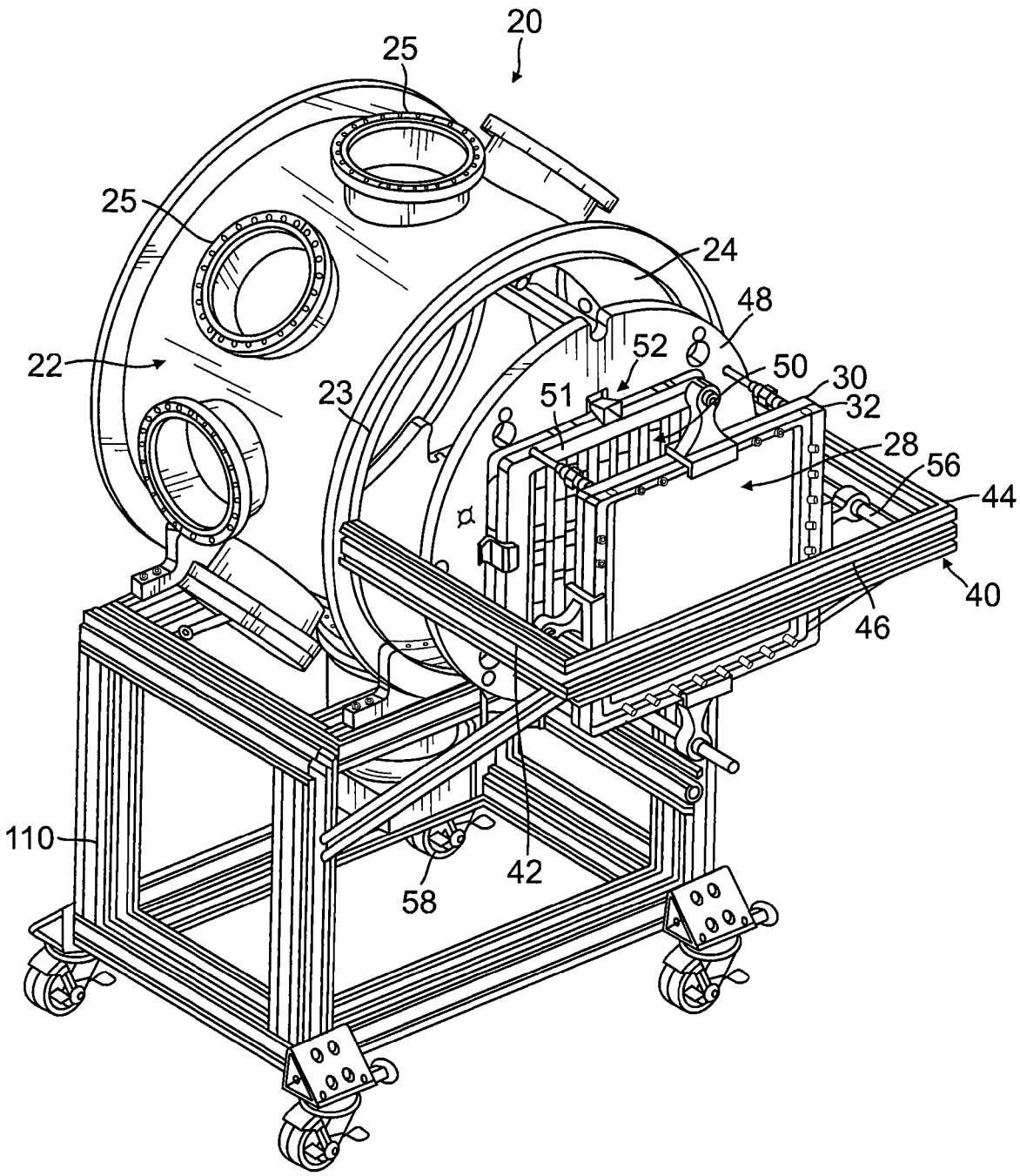
FIG. 1 is a perspective view of a test chamber having features of the present invention, shown at a stage during which the chamber is opened and components are being loaded into it.
Figure 2:
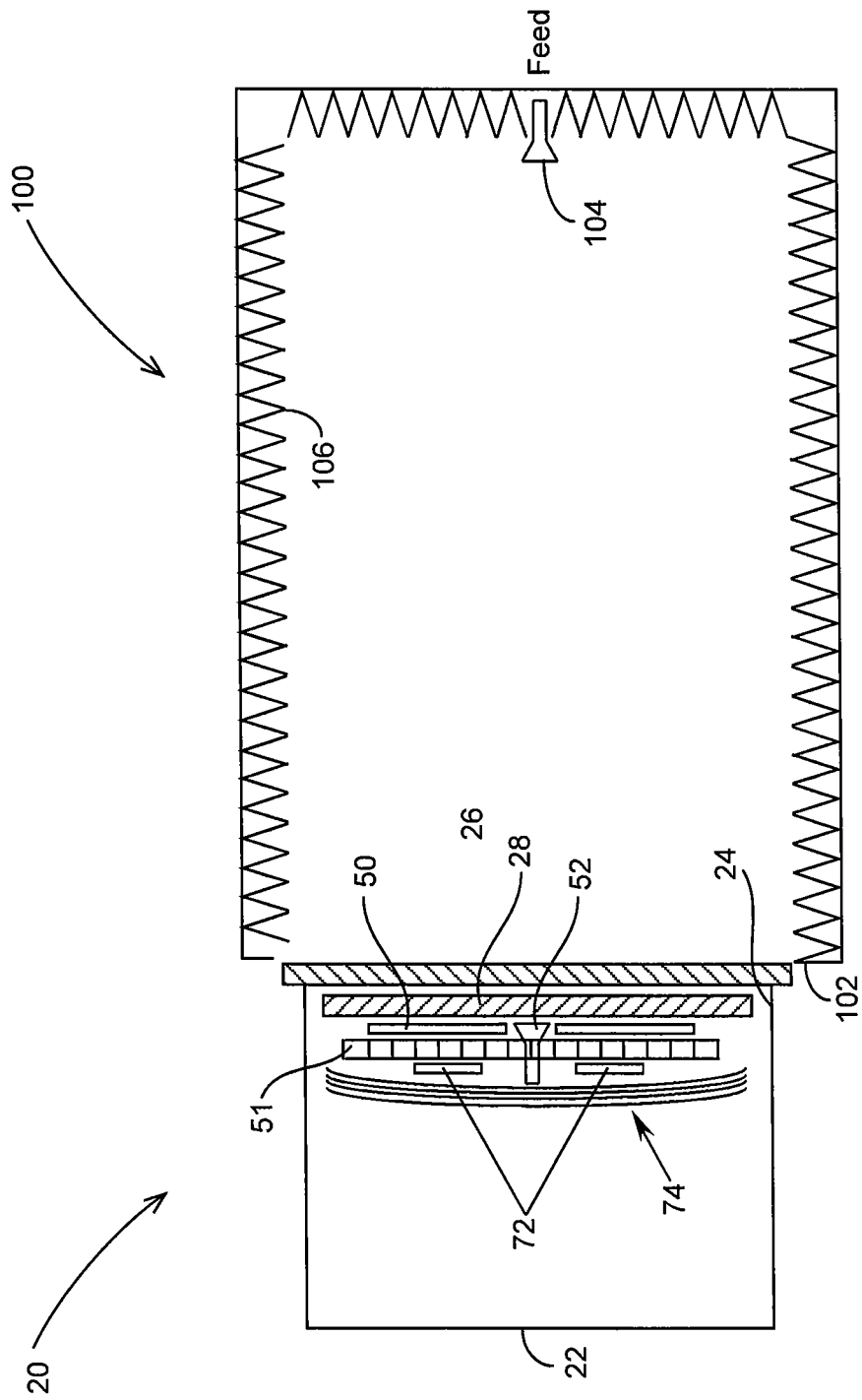
FIG. 2 is a schematic view from above of the test chamber of FIG. 1, shown after components have been loaded and showing the spatial relation of various components.

In a first aspect, and with reference to FIGS. 1 and 2, the test chamber 20 of the preferred embodiment defines a housing 22, configured to be evacuated to a space-like pressure. Preferably, the housing is configured generally in the shape of a cylinder, and may be formed from metal, such as stainless steel, and is further configured to receive within its interior electronic components that will be subjected to test protocols which simulate use requirements in space. In preferred embodiments, the cylinder may be between 2.5 feet and 4.5 feet in diameter, and between two and four feet deep.

As seen in FIG. 1, the preferably cylindrical housing 22 has an insert opening 24, through which the electronic components for testing may be inserted. In a preferred embodiment, the insert opening 24 comprises an entire planar end of the cylindrical shape of the housing. The opening 24 is closable by a closure system. The chamber should be sealed sufficiently to permit atmospheric evacuation of the chamber to reach the aforementioned space-like pressures, and thus to permit testing to begin when radio communication will be established with the device under test within the chamber. In addition to the insert opening 24, a plurality of additional smaller openings 25 may be provided in the housing into which test operators may insert their arms and hands for manipulating and adjusting the configuration and settings of components that have been installed within. These openings 25 will be sealed during testing.

In a preferred embodiment, the closure system is substantially transparent to radio frequencies; it is capable of being cooled to space-like temperatures, and thereby capable of imparting cooling to the electronic components under test; and, it is capable of sealing the chamber and thereby permitting a low pressure or vacuum condition to be developed in the chamber.

Accordingly, the closure system preferably comprises two main components, schematically seen together in FIG. 2: first, a pressure window 26, and second, a thermal window 28, which in combination provide the desired results. Both the pressure window 26 and the thermal window 28 are formed from material that is radio frequency ("RF") transparent, preferably polycarbonate, in a physical configuration that is described in detail more fully below. Although polycarbonate is a preferred material, other RF transparent materials may be used.

Pressure Window

The pressure window 26, in a preferred embodiment, may be configured as a single sheet of polycarbonate which may be placed in abutment with the edges 23 of the opening 24 to seal the chamber 20. A flexible gasket (not shown) may be positioned between the edges of the chamber forming the opening 24, and the edges of the pressure window 26 to facilitate the ultimate development of a vacuum condition in the chamber during the device testing stage when a pump evacuates air from the chamber. As the chamber approaches a vacuum condition, the gasket forms a seal between the pressure window and the edge of the opening. In a preferred embodiment, the pressure window 26 is made of polycarbonate and its thickness may be about three inches (about 7.5 cm). In order to fit the chamber 22 of the preferred embodiment, it may have a circular shape.

Thermal Window

Figure 3:
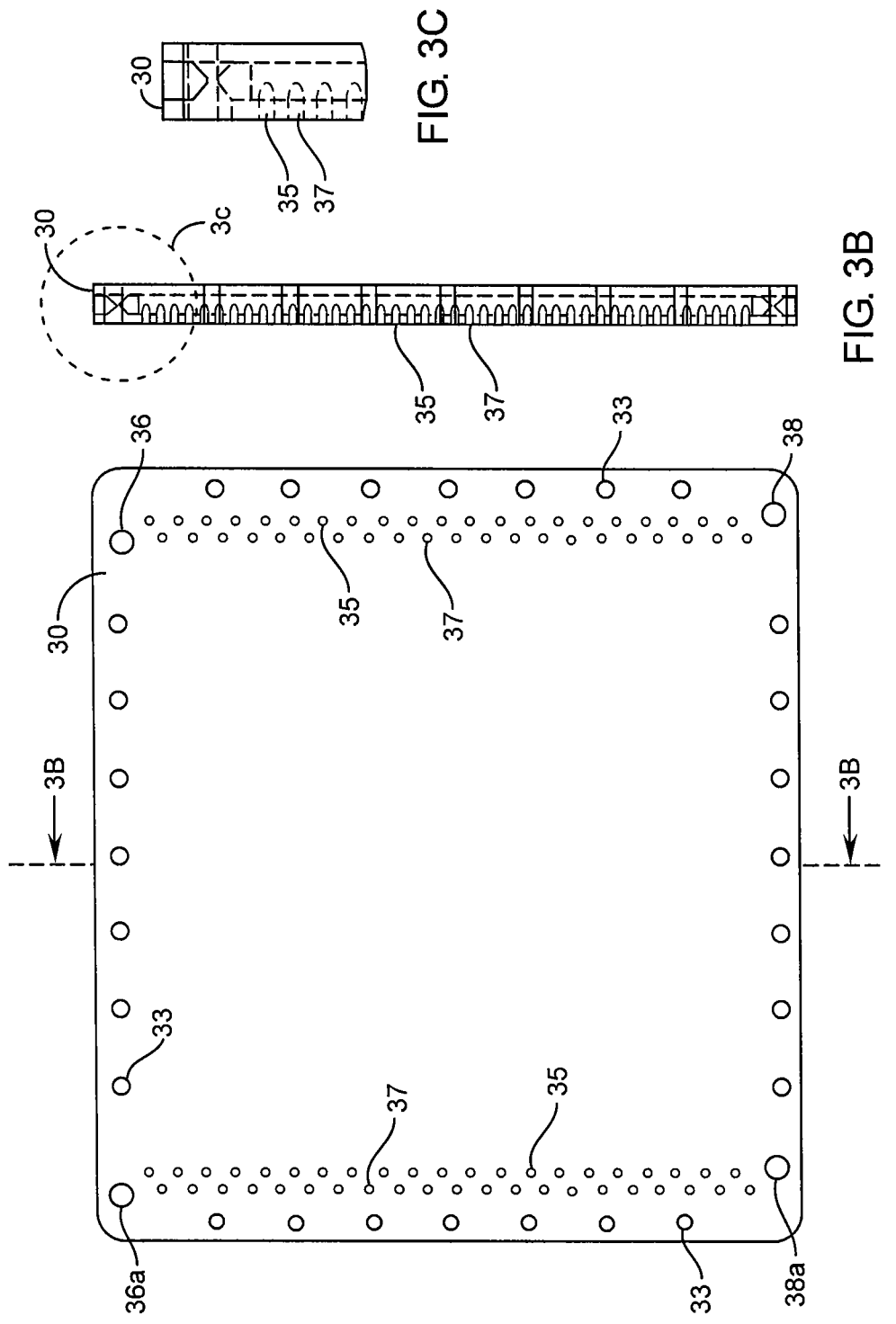
FIG. 3A is an elevational view of a manifold plate that forms a component of a thermal window of the present invention.
FIG. 3B is a sectional view of FIG. 3A, taken substantially along the line 3B.
FIG. 3C is a detail of FIG. 3B.
Figure 4:
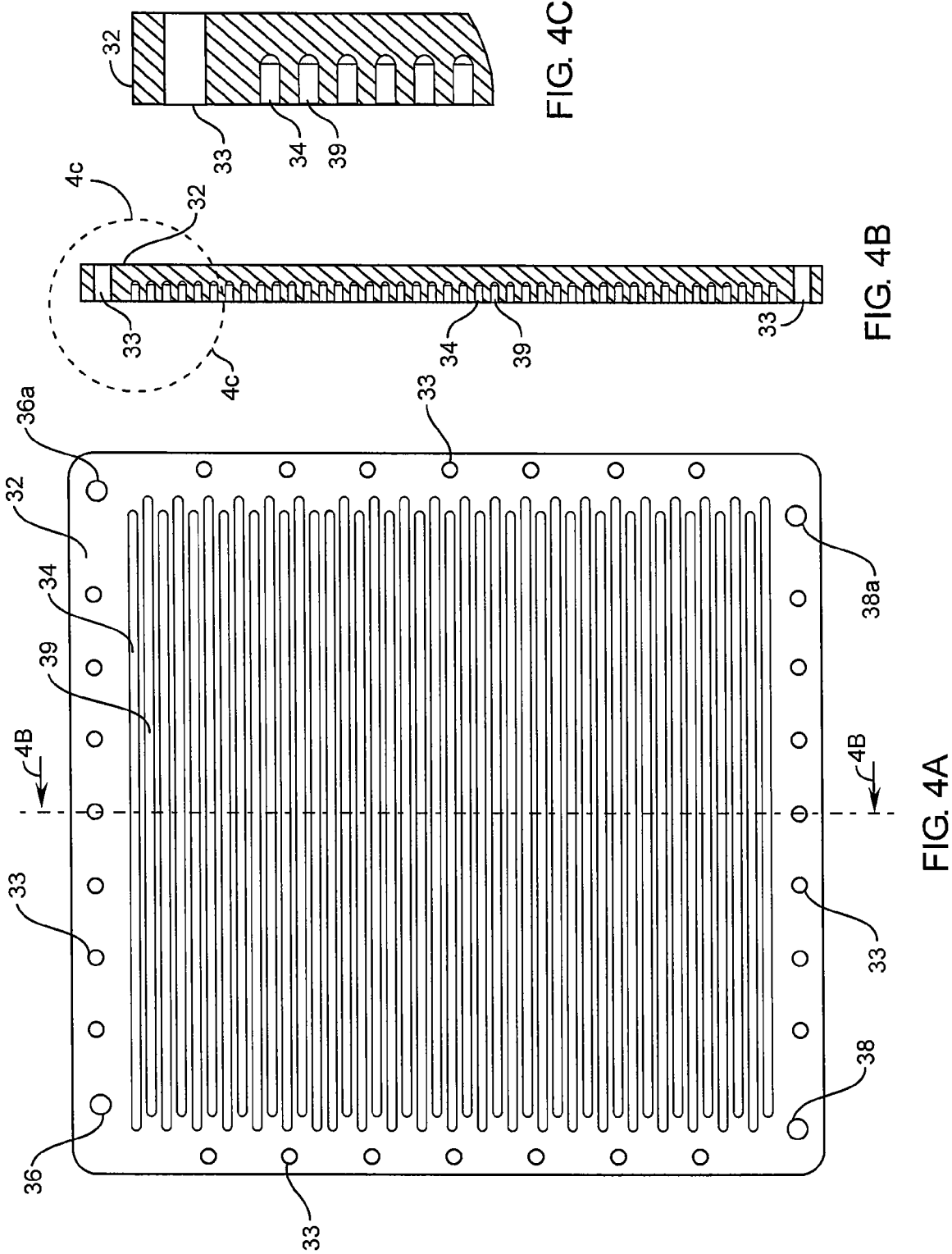
FIG. 4A is an elevational view of a channel plate that forms another component of a thermal window of the present invention.
FIG. 4B is a sectional view of FIG. 4A, taken substantially along the line 4B.
FIG. 4C is a detail of FIG. 4B.
Figure 5:
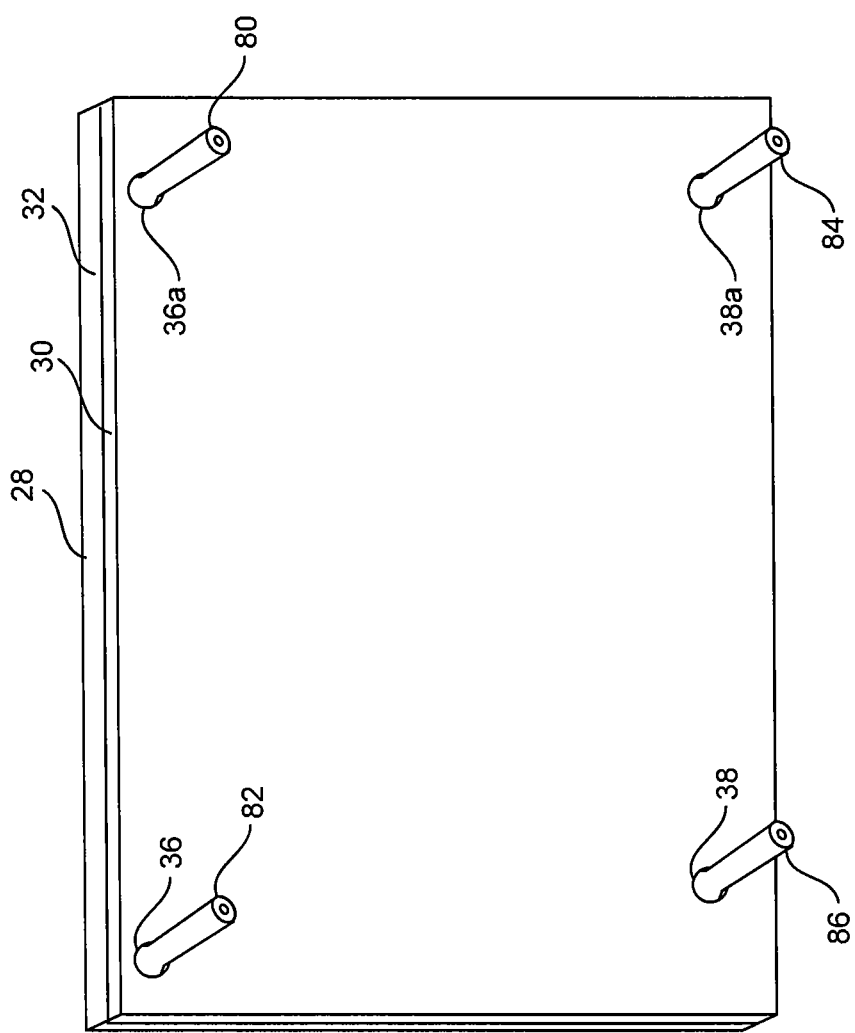
FIG. 5 is a perspective view of a thermal window of the present invention, showing inlet and outlet legs connected to the window to facilitate the flow of cooling fluid.

In a preferred embodiment exemplified in FIGS. 3-5, the thermal window 28 is formed of two plates of polycarbonate in laminate form, an inner plate 30 (exemplified in FIGS. 3A-3C), and an outer plate 32 (exemplified in FIGS. 4A-4C) which are placed in abutting contact with each other and affixed to each other. Significantly, the laminated plate configuration is cut or machined to have runways or channels along a surface of at least one of the plates (preferably the outer plate, or "channel plate") so that when the opposing plate (preferably the inner plate or "manifold plate") is placed in abutment, a series of closed conduits 34, 39 extend in a planar profile throughout the interior of the thermal window 28. In a preferred embodiment, each plate of polycarbonate may be between 0.5 inches and 2.0 inches thick.

These conduits 34, 39 possess at least one entry opening 36, and one exit opening 38, whereby cooling fluid from a heat exchanger (not shown) may be directed to flow through the conduits 34, 39 via the openings to cool the entire window 28. In a preferred embodiment, the channels may possess additional entry openings 36a and additional exit openings 38a, (FIG. 4A) so that at least two independent conduits 34, 39 are provided to carry cooling fluid through the window 28 independently of each other.

Preferably, the two independent conduits 34, 39 are configured so that the fluid flow direction in each conduit is in opposite directions. A plurality of independent conduits will tend to provide for greater uniformity in the temperature that may be achieved across the extent of the window 26 than a single conduit. A plurality of shorter conduits in which cooling fluid is directed will each tend to have a smaller temperature difference along the length of the conduit than a single longer conduit. Further, where conduits are arranged so that the cooling fluid runs in opposite directions in each conduit, this will further add to the uniformity of surface temperature across the extent of the thermal window. A uniform temperature across the window is desirable because such uniformity more accurately simulates the conditions in space that will eventually be applied to the components subject to testing in the chamber.

In a preferred embodiment, the conduits are configured to have a substantially uniform configurations that intertwine with each other to produce a highly uniform flow across the window. This intertwining configuration may be arranged by linking the horizontally extending channels of a first conduit 34 in the channel plate 32 via a first set of connecting channels 35 in the manifold plate 30, and the horizontally extending channels of a second conduit 39 in the channel plate 32 via a second set of connecting channels 37 in the manifold plate 30.

In further preferred aspects of the thermal window 28, the two plates 30, 32 are connected to each other by applying an epoxy adhesive or other suitable adhesive means. Additionally, a plurality of pin holes 33 may be drilled in opposing surfaces of the plates; pins may be inserted in the holes to span between the two plates, in order to reduce shear forces that might develop across the plates and that might otherwise tend to develop in the epoxy adhesive. In this configuration, the epoxy adhesive may be placed under almost pure tensile force holding the plates together, while shear forces may substantially be taken by the pins.

In yet a further preferred aspect of the thermal window 26, exemplified in FIG. 5, once the two plates 30, 32 are securely attached to each other to form a laminar structure, inlet legs 80, 82 and exit legs 84, 86 are inserted into inlet holes 36a, 36 and outlet holes 38a, 38 respectively so that they protrude perpendicularly from the thermal window 28. The point of insertion of each leg into the window 26 is sealed with a suitable hardening compound such as an epoxy or silicone sealant so as to permit cooling fluid to flow via the legs through the conduits 34 in the thermal window 28 without fluid pressure loss. These protruding legs are configured to engage with fluid supply and extraction conduits that are connected to a fluid heat exchanger (not shown), when the chamber 20 is loaded with equipment for testing.

Loading the Chamber with Components for Use

In application of the test chamber, a preferred method of loading the chamber with components and with devices for testing may be accomplished. As may be seen in FIG. 1, with the removal of the pressure window, an empty cylindrical-shaped chamber 20 is ready to be loaded with equipment and components for testing. A horizontal U-shaped railing 40 is provided to slide in and out of the housing 22 on runway channels (not shown) in the housing wall, to facilitate inserting and stabilizing the equipment in the chamber. The railing comprises two parallel opposing rails 42, 44, and a connecting rail 46. A circular disc shaped support structure 48 spans across the distal end of the railing 40, to support the weight of some of the equipment to be loaded. To the support structure 48 there is attached a specialized bracket 51, depending on the type of device 50 that is to be tested, which serves as a direct support for electronic components 50 to be tested (FIG. 2). A calibration horn 52, whose function will be explained below, is also attached to the support structure. The specialized bracket 51 acts as a support structure for the devices to be tested 50. These devices are attached with the planar antennae of the devices to be tested 50 facing outwards (i.e., proximally) towards the thermal window 28 and the pressure window 26 of the closure system.

At the proximal end of the U-shaped railing 40, the thermal window 28 is supported between two supplemental rails (one of the supplemental rails, on the left, is not visible in FIG. 1, while the other rail 56 on the right, is visible). The supplemental rails are each, in turn, supported by the parallel rails 42, 44. Once the required equipment is loaded in this fashion, the thermal window 28 is slid on the supplemental rails until the thermal window 28 is positioned adjacent the device to be tested 50. (As used herein, the term "adjacent" shall be used to convey a relationship of being proximate or close to another object, but not in contact with that object.) The thermal window is not in contact with the device 50 so there will be no conduction of heat from the device, and a substantially uniform thermal gradient can be maintained across the window surface during the cooling cycle. During the cooling cycle, radiant heat transfer may occur from the device to the thermal window.

Thereafter, the U-shaped rail 40 is slid into the housing carrying all components with it in unison so that all the components are slid into the housing. Upon being slid distally into the housing, the legs 80, 82, 84, 86 (FIG. 5) of the thermal window 28 are configured to engage with receiving ports which will connect the fluid line extending through the thermal window with a heat exchanger (not shown). Thereafter, the connecting rail 46 is removed, so that the full external surface of the thermal window 28 is exposed to the opening 24 without any obstruction. The pressure window 26 is then installed to close the opening 24, and may be initially clamped in position. A circular gasket may be placed between the pressure window 26 and the edges 23 of the opening 24 to facilitate formation of a vacuum in the chamber. After a vacuum pump 58 has established a near vacuum inside the chamber, the clamps may be removed because the atmospheric force on the pressure window 26 created by the vacuum will be sufficient to hold the pressure window 26 in position. Testing of the devices 50 may begin.

It will be readily appreciated that, for tests of further devices 50, it will only be necessary to remove the pressure window 26, slide out the rails 42, 44, separate the thermal window 28 by sliding it outwards on supplemental rails 54, 56, and then exchange the devices to be tested. Thereafter the system may be closed using the same sequence of steps as before.

Final Configuration

Thus, the final configuration of the chamber 20 sealed and loaded with devices 50 for testing is preferably as configured in FIG. 2, described as follows. Moving from the outside inwards, there is the pressure window 26, acting to seal the chamber while being radio frequency transparent made of polycarbonate. Adjacent the pressure window 26 is the thermal window 28, also radio frequency transparent being made of laminar sheets of polycarbonate, and cooled by internally flowing cooling fluid. Adjacent the thermal window, the devices to be tested 50 are suspended against suitable support structure such as a bracket 51. Typically, it is the antennae of the devices to be tested that must be cooled to the lowest temperatures during testing. These antennae typically have a planar form. Therefore, the planar antennae are positioned adjacent the preferably planar thermal window 28, so that the maximum amount of heat transfer may take place between antenna and thermal window which acts as a heat sink. The rest of the device 50 under test will be positioned on the side of the antenna away from the thermal window against the bracket 51. Thus, as a result of this configuration, radio frequency waves may be directed from outside the chamber 20 in a straight line to the antennae of the devices under test 50, such that the radio waves are obstructed only by the RF transparent pressure window 26 and the RF transparent thermal window 28, and by no other components or device elements.

Behind (i.e., distal to) the devices to be tested is the specialized support structure or bracket 51. Behind that, heat sources 72 may be mounted which may be required when certain types of equipment is tested where localized heating may be expected from the various components in the space craft. Thus, these heat sources assist in the accurate simulation of the conditions that will be encountered in space. Behind the heat sources 72, a multi-layered insulation 74 may be positioned to seal off the back of the chamber, and to insulate and maintain the thermal stability of the entire unit.

Environmental Test Conditions

Once the chamber 20 is fully loaded, and the pressure window 26 installed as exemplified in FIG. 2, the vacuum pump 58 may be activated to evacuate the chamber. Before, during, or after decompression of the chamber, cooling fluid 28 may be pumped through the conduits in the window 28 to commence bringing the thermal window 28 to its lowest equilibrium temperature. Under the vacuum pressure in the chamber, any heat in the devices 50 under test is not lost to the thermal window through conduction (which requires the presence of air), but is lost through radiation. After a period of time the proximity of the devices 50 to the thermal window 28 causes each device to approach an equilibrium temperature which is substantially the same in each component. The flat surface of the window 28, preferably being larger than the devices 50 under test, facilitates "extracting" radiant heat from the flat devices/antennae under test, and lowering their temperature.

As illustrated in the configuration exemplified in FIG. 2, the devices 50 under test are exposed to a clear window through the opening in the chamber, in which the only material that separates the devices from the outside is polycarbonate, in the form of the thermal window 28 and the pressure window 26. Thus, once the chamber 20 is loaded with its contents and the pressure window 26 is attached to the edges of the opening 24 to seal the chamber, the chamber 20 itself is moved up on a wheeled cart 110 (FIG. 1) to an anechoic chamber 100 of known configuration, and exposed to the interior of the anechoic chamber through a window 102 therein, as exemplified in FIG. 2. An anechoic chamber is a known device designed to stop reflections of either sound or electromagnetic waves using baffles 106 made of carbon covered protrusions and the like. They may also insulate from exterior sources of noise, which means they simulate a quiet open-space of infinite dimension, which is useful when exterior influences would otherwise give false results. In a preferred embodiment of the invention, an radio frequency transmitter/receiver 104 or "feed" is provided at an end of the anechoic chamber opposite the chamber 20. Thus radio communication may be established between the feed 104 and the antennae of the devices 50 under test in the chamber 20, where polycarbonate in the pressure and thermal windows is the only material separating the feed and the devices. In order to "tune" the feed 104, the calibration horn 52 is located on the support 48 at exactly the same distance from the feed 104 as the devices to be tested 50. This enables the feed to be tuned using the calibration horn 52 prior to closing the pressure window 26 and evacuating the chamber.

Example of Tests Applied to Window, and Results Thereof

Figure 6:
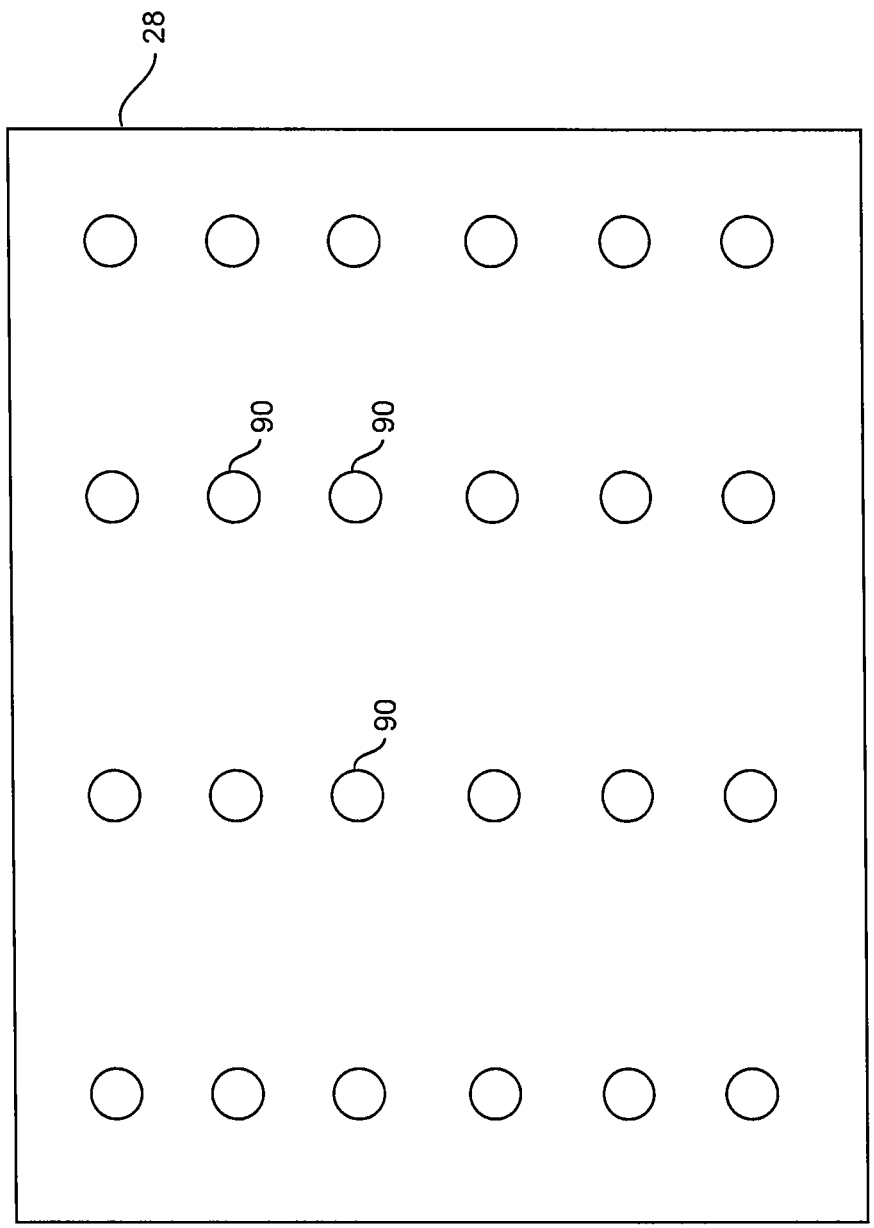
FIG. 6 is an elevational view of a thermal window having features of the present invention, showing the position of thermocouples placed for testing the operability of the thermal window.

An example is now provided in which the thermal window 28 was tested for response to cooling. In conducting this test, a plurality of thermocouples 90 (in effect, electronic thermometers) were attached to the exposed surface of the thermal window 28, in a configuration that is schematically shown in FIG. 6.

As previously discussed, the thermal window 28 is not in contact with the device under test 50, so there in no conductive heat transfer from the device. And when the interior of the chamber is in its vacuum condition, there is effectively no atmospheric conduction of heat. In these circumstances, a substantially uniform thermal gradient can be maintained across the window surface during the cooling cycle in which cooling fluid is pumped through the conduits within the thermal window. During the cooling cycle, radiant heat transfer may occur from the device 50 to the thermal window 28.

Figure 7:
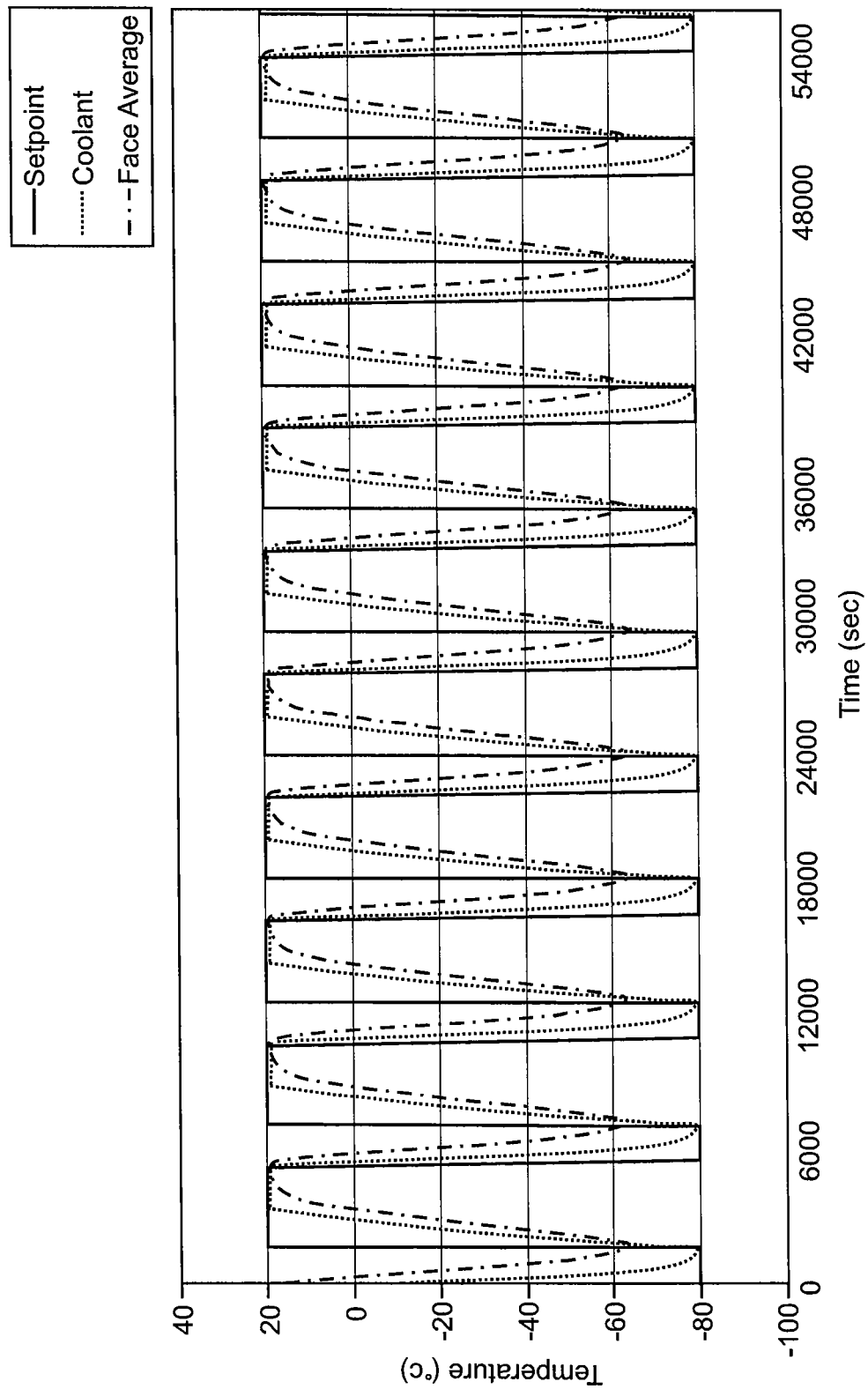
FIG. 7 is a graph showing test results obtained during thermal testing of the thermal window.

In a first aspect of the test protocol applied to the window 28, the window was subjected to fairly aggressive cyclical temperature loading in order to ascertain the response of the window. Cooling fluid was pumped through the conduits 34 under a cyclical sequence that is graphically exemplified in FIG. 7. In cycles lasting about 90 minutes each, the "set point" of the chiller was set to start at 20° C., and held constant for about 60 minutes. The set point then was caused to fall to minus 80° C. and held constant for about 30 minutes before the set point reverted to 20° C. thus completing the cycle. Using the thermocouples 90 affixed to the surface of the window 28, the face average temperature of the window surface was monitored as the temperature of the coolant rose and fell. The results are reflected in FIG. 7 which demonstrate that, while the temperature of the coolant reaches the lower set point of minus 80° C. in about 30 minutes seconds, the face average temperature of the window reaches minus 65° C.

in the same amount of time. Also, when the set point reverts to 20° C., the coolant temperature is elevated to reach the same temperature in about 30 minutes, while the face average reaches the set point in about 40 minutes. Thus, the face average responds rapidly to a fall or rise in fluid temperature, and provides an efficient system for cooling an environment. Because thermocouples will not be affixed to the thermal window 28 when the vacuum chamber is sealed to test the devices 50, these curves may be used to estimate the temperature of the thermal window based on measurement of the coolant temperature over time.

Figure 8:
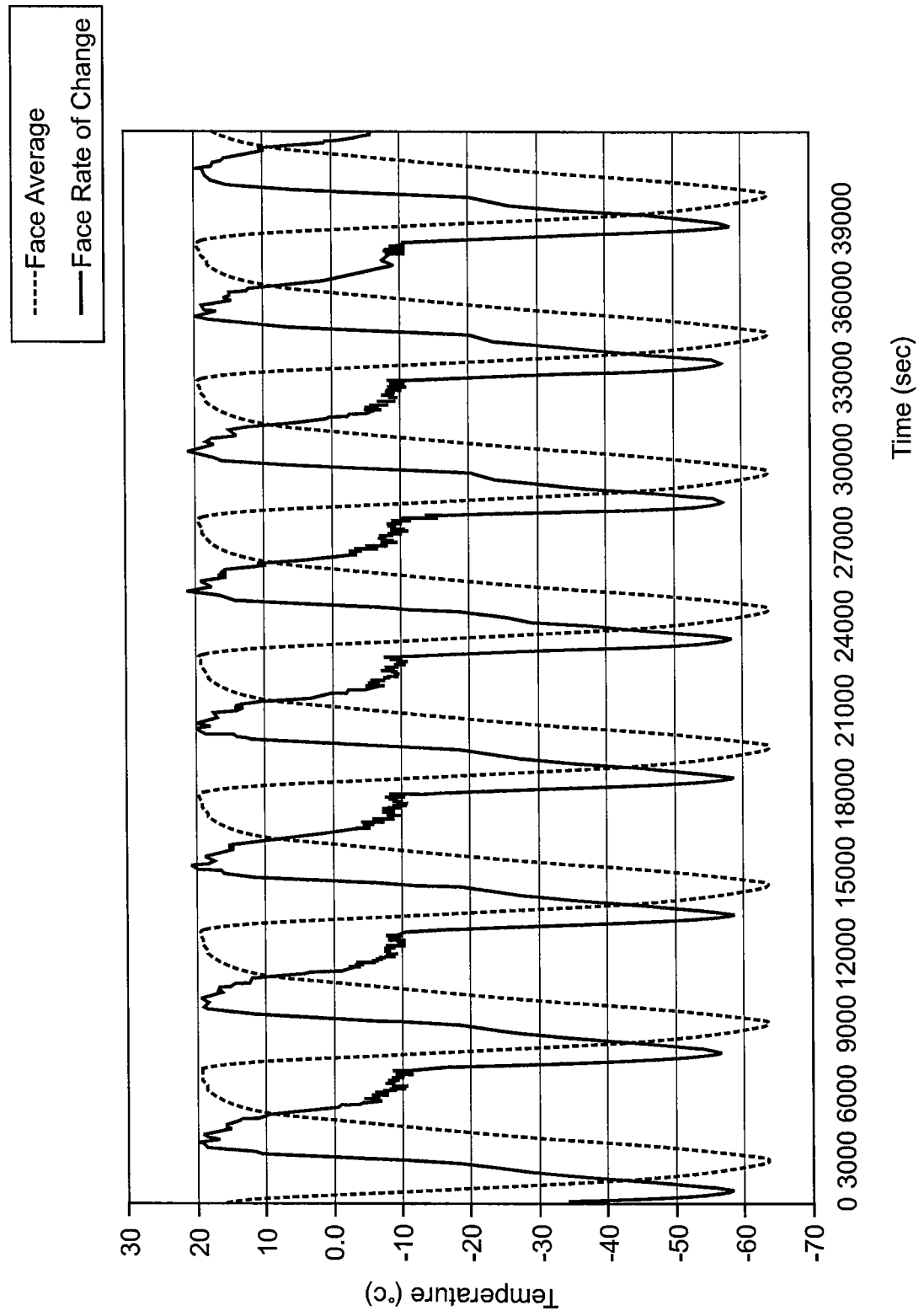
FIG. 8 is a graph showing further test results obtained during thermal testing of the thermal window.

Additionally, using the same test protocol but extracting different data, FIG. 8 shows a plot of how the rate of change (degrees/min) of the thermal window face temperature changes during the test cycles, and demonstrates the response rate of the window to changes in temperature of the cooling fluid. Again, these results demonstrate an efficient and effective cooling window where the circumstances require efficient and transparent RF communication with a device under test that is being subjected to cooling.

Finally, further measurements taken by the thermocouples 90 on the window face show that, during the cooling cycle, the thermal gradient across the length and breadth of the window surface is effectively negligible. This conclusion was arrived at after a 30 day qualification test, during which time the window was put through the cycling temperatures indicated in FIG. 7. The very small thermal gradient further demonstrates the suitability of the thermal window 28 for simulating a highly uniform thermal environment such as is likely to be encountered in space.

When the entire sealed chamber 20 was used in its final configuration, and electronic devices 50 were tested for radio frequency communication under space-like temperature and pressure conditions, it was found that a loss of 0.5 dB to 1 dB relative to a free space transmission of the same distance and frequency was experienced. As those of skill will appreciate, this degree of loss is insignificant in the context of the test environment, and the system as a whole was determined to possess the qualities required for testing devices under radio communication in a space-like environment.

Thus, there is described an advantageous and novel solution to a problem encountered in the prior art that greatly improves systems and methods for testing electronic components destined for use in space. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A chamber for testing electronic devices, comprising:
a housing defining an opening;
a pressure window configured to close the opening under a pressure seal, the pressure window being formed of a substantially radio-frequency transparent material; and
a thermal window positioned inside the housing, the thermal window defining one or more internal conduits for the passage of cooling fluid, the thermal window being formed of a substantially radio-frequency transparent material,
wherein, the pressure window and the thermal window are positioned in relation to each other such that a radio frequency signal is able to pass from outside the housing directly through both the pressure window and the thermal window into the housing.

2. The chamber of claim 1, wherein, for both the thermal window and the pressure window, the substantially radio-frequency transparent material is polycarbonate.

3. The chamber of claim 1, wherein the thermal window is formed as a laminate from two sheets bonded together.

4. The chamber of claim 1, further including a pump configured to pump air from the housing sufficiently to create a vacuum condition within the housing.

5. The chamber of claim 1, wherein the one or more internal conduits in the thermal window includes at least two independent conduits wherein cooling fluid in one independent conduit flows in a direction opposite to the flow of cooling fluid in another independent conduit.

6. An apparatus for testing an electronic device, comprising:
   a housing capable of maintaining a vacuum condition within;
   a thermal window positioned inside the housing, the thermal window defining one or more internal conduits for the passage of cooling fluid, and being formed of a substantially radio-frequency transparent material whereby the thermal window is capable of transmitting a radio frequency signal from outside the housing through the thermal window for communication with the device;
   wherein the one or more internal conduits in the thermal window include at least two independent conduits wherein cooling fluid in one independent conduit flows in a direction opposite to the flow of cooling fluid in another independent conduit.

7. The apparatus of claim 6, further comprising a support bracket for holding a device to be tested proximate to the thermal window within the housing.

8. The apparatus of claim 7, wherein the thermal window is positionable in a fixed position to be proximate to an antenna of the device when the device is supported on the bracket.

9. The apparatus of claim 6, wherein the substantially radio-frequency transparent material is polycarbonate.

10. The apparatus of claim 6, wherein the thermal window is formed as a laminate formed from a channel plate and a manifold plate that are bonded together.

11. The apparatus of claim 6, further including a separate pressure window configured to close the housing under a pressure seal to achieve a vacuum condition within the housing, the pressure window being formed of a substantially radio-frequency transparent material, and the thermal window is positioned inside the chamber and separate from the pressure window.

12. A method of testing comprising:
    positioning a device having an antenna within a chamber having an opening;
    positioning a cooling element proximate to the antenna wherein the cooling element is substantially transparent to radio frequency,
    closing the opening with a pressure window that is substantially transparent to radio frequency;
    evacuating the chamber to a low pressure;
    passing a cooling fluid through channels inside the cooling element to lower the temperature of the cooling element, thereby cooling the antenna of the device; and
    sending radio frequency signals from an antenna outside the chamber, through the pressure window and through the element, to the cooled antenna inside the chamber;
    thereby, applying test protocols to the device by radio frequency signal.

13. The method of claim 12, further including positioning the chamber proximate to an anechoic chamber so that the opening faces into the anechoic chamber.

14. The method of claim 13, wherein sending radio frequency signals from an antenna outside the chamber includes sending the radio frequency signals through the anechoic chamber.

15. The method of claim 12, wherein passing a cooling fluid to lower the temperature of the cooling element includes lowering the temperature to at least minus 65° C.

16. The method of claim 12, wherein positioning the cooling element proximate to the antenna includes positioning an element that is shaped to conform to the shape of the antenna.

17. The method of claim 16, wherein the cooling element has a planar configuration.

18. The method of claim 16, wherein the pressure window is separate from the cooling element.

* * * * *